（12) United States Patent
Thueer et al.

(10) Patent No.: US 9,072,841 B2
(45) Date of Patent: Jul. 7, 2015

(54) MEDICATED MODULE WITH AUTOMATIC RESERVOIR ENGAGEMENT

(75) Inventors: Thomas Urs Thueer, Oxfordshire (GB); David Richard Mercer, Warwickshire (GB); Garen Kouyoumjian, Warwickshire (GB); Malcolm Stanley Boyd, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/988,989

(22) PCT Filed: Nov. 28, 2011

(86) PCT No.: PCT/EP2011/071140
§ 371 (c)(1),
(2), (4) Date: May 22, 2013

(87) PCT Pub. No.: WO2012/072563
PCT Pub. Date: Jun. 7, 2012

(65) Prior Publication Data
US 2013/0237932 A1 Sep. 12, 2013

(30) Foreign Application Priority Data

Nov. 29, 2010 (EP) ..................................... 10192996

(51) Int. Cl.
*A61M 31/00* (2006.01)
*A61M 5/32* (2006.01)
(Continued)

(52) U.S. Cl.
CPC ........... *A61M 5/3294* (2013.01); *A61M 5/2448* (2013.01); *A61M 5/2466* (2013.01);
(Continued)

(58) Field of Classification Search
CPC . A61M 3/005; A61M 5/158; A61M 5/16827; A61M 5/19; A61M 5/2066; A61M 5/2448; A61M 5/284; A61M 5/3134; A61M 5/31596; A61M 5/32; A61M 5/3202; A61M 5/321; A61M 5/3294; A61M 5/3243; A61M 5/3269; A61M 5/3271; A61M 5/3272; A61M 5/3276; A61M 2005/1787; A61M 2005/208; A61M 2005/2448; A61M 2005/2451; A61M 2005/3236; A61M 2005/3263; A61M 5/2466; A61M 5/3146; A61M 5/326; A61M 5/347; A61M 2005/247; A61M 2005/2474; A61M 2005/3247; A61M 2005/3267; A61M 2205/581; A61M 2205/584
USPC ............ 604/93.01, 82, 86, 88, 110, 134, 135, 604/136, 137, 138, 139, 181, 187, 192, 193, 604/194, 195, 196, 197, 198, 201, 202, 203, 604/204, 205, 228, 232, 234, 264, 272
See application file for complete search history.

(56) References Cited

U.S. PATENT DOCUMENTS 5,251,198 A 10/1993 Strickler
6,001,801 A 12/1999 Coy et al.
(Continued)

FOREIGN PATENT DOCUMENTS

CN 1154657 A 7/1997
(Continued)

OTHER PUBLICATIONS

International Preliminary Report on Patentability for PCT/EP2011/071140 dated Jun. 13, 2013.
(Continued)

*Primary Examiner* — Bhisma Mehta
*Assistant Examiner* — Nicholas Meghri
(74) *Attorney, Agent, or Firm* — McDonnell Boehnen Hulbert & Berghoff LLP

(57) ABSTRACT

A medicated module for an injection system to co-deliver at least two medicaments is disclosed where a primary delivery device containing a primary medicament accepts a medicated module containing a single dose of a secondary medicament and where both medicaments are delivered through a hollow needle. The medicated module does not require the user to manually engage a reservoir containing the secondary medicament. Instead, a biasing member automatically activates the reservoir when the needle guard is retracted. The needle guard prevents accidental needle sticks before and after an injection, and locks after dose delivery.

12 Claims, 4 Drawing Sheets

(51) Int. Cl.
*A61M 5/24* (2006.01)
*A61M 5/31* (2006.01)
*A61M 5/34* (2006.01)
*A61M 5/178* (2006.01)

(52) U.S. Cl.
CPC .............. *A61M5/3146* (2013.01); *A61M 5/326* (2013.01); *A61M 5/347* (2013.01); *A61M 2005/1787* (2013.01); *A61M 2005/247* (2013.01); *A61M 2005/2474* (2013.01); *A61M 2005/3247* (2013.01); *A61M 2005/3267* (2013.01); *A61M 2205/581* (2013.01); *A61M 2205/584* (2013.01)

(56) References Cited

U.S. PATENT DOCUMENTS

| | | | |
|---|---|---|---|
| 6,090,070 | A | 7/2000 | Hager et al. |
| 6,562,002 | B1 * | 5/2003 | Taylor ............................ 604/82 |
| 2002/0004648 | A1 | 1/2002 | Larsen et al. |
| 2002/0007142 | A1 | 1/2002 | Hjertman et al. |
| 2005/0165363 | A1 * | 7/2005 | Judson et al. ................. 604/209 |
| 2006/0276755 | A1 | 12/2006 | Sullivan et al. |
| 2008/0262436 | A1 * | 10/2008 | Olson ............................ 604/198 |
| 2009/0018506 | A1 | 1/2009 | Daily et al. |

FOREIGN PATENT DOCUMENTS

| | | |
|---|---|---|
| CN | 1507360 A | 6/2004 |
| WO | 0176665 A1 | 10/2001 |
| WO | 0189613 A1 | 11/2001 |

OTHER PUBLICATIONS

Office Action issued in Chinese Patent Application No. 2014090101193540 dated Sep. 4, 2014.

Machine Translation of WO 01/76665 A1, Publication Date: Oct. 18, 2001.

* cited by examiner

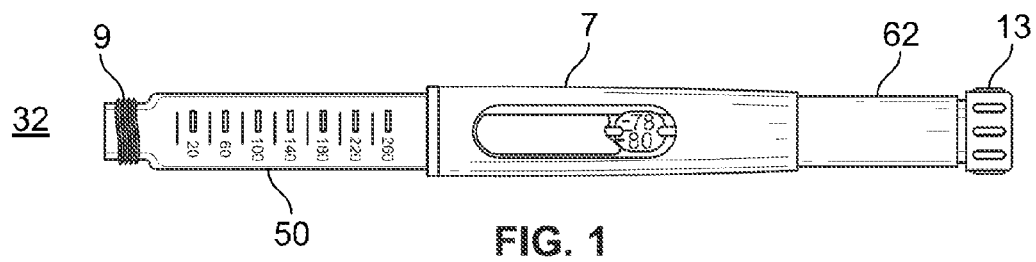
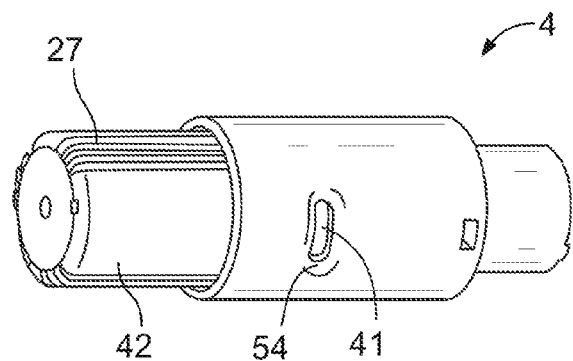
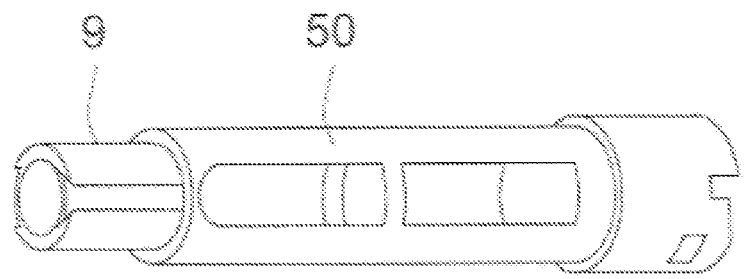

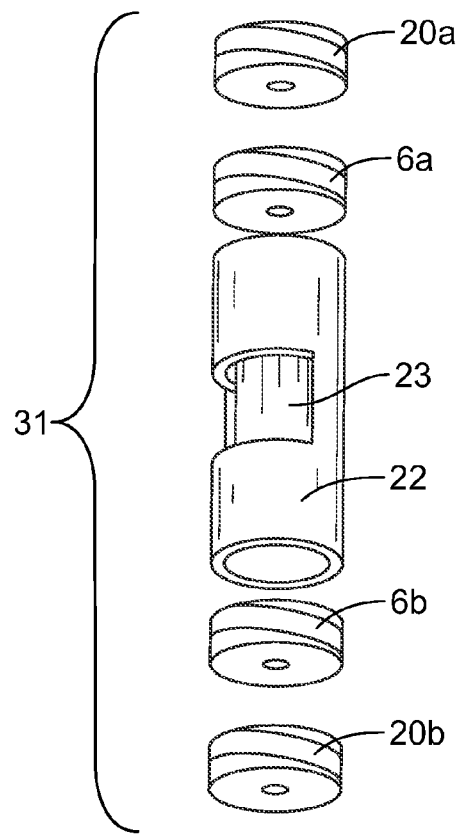
FIG. 10
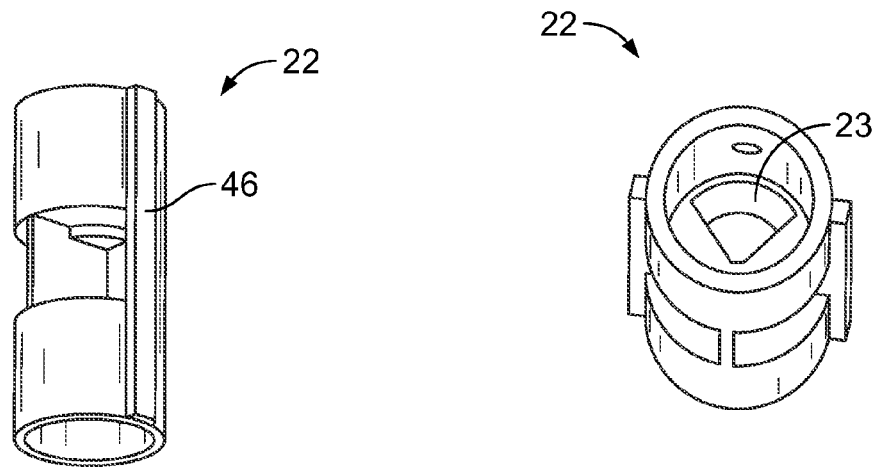
FIG. 11
FIG. 12

MEDICATED MODULE WITH AUTOMATIC RESERVOIR ENGAGEMENT

CROSS REFERENCE TO RELATED APPLICATIONS

The present application is a U.S. National Phase Application pursuant to 35 U.S.C. §371 of International Application No. PCT/EP2011/071140 filed Nov. 28, 2011, which claims priority to European Patent Application No. 10192996.6 filed Nov. 29, 2010. The entire disclosure contents of these applications are herewith incorporated by reference into the present application.

FIELD OF INVENTION

This invention relates to medical devices and methods of delivering at least two drug agents from separate reservoirs using devices having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, our invention concerns a medicated module where the user does not have to manually select or set the module to dispense the second drug agent. Activation of the needle guard automatically causes the reservoir of secondary medicament to engage with dispensing conduits to allow a set dose of primary medicament and a single fixed dose of the of the secondary medicament to be injected. Our invention is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. This invention is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

SUMMARY

Accordingly, there exists a strong need to provide devices and methods for the delivery of two or more medicaments in a single injection or delivery step that is simple for the user to perform. Our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Our invention also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

Our invention also provides a medicated module that automatically causes the reservoir of secondary medicament to come into fluid communication with the primary medicament upon activation of the needle guard. This eliminates the need for the user to manually set or adjust the medicated module after performing a priming step. These and other advantages will become evident from the following more detailed description of the invention.

Our invention allows complex combinations of multiple drug compounds within a single drug delivery system. The invention allows the user to set and dispense a multi-drug compound device though one single dose setting mechanism and a single dispense interface. This single dose setter controls the mechanism of the device such that a predefined combination of the individual drug compound is delivered when a single dose of one of the medicaments is set and dispensed through the single dispense interface.

By defining the therapeutic relationship between the individual drug compounds our delivery device would help ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect this invention is of particular benefit to users with dexterity or computational difficulties as the single input and associated predefined therapeutic profile removes the need for them to calculate their prescribed dose every time they use the device and the single input allows considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin. In one embodiment of our invention there is provided a medicated module attachable to a drug delivery device that comprises an outer housing having an inner surface, a proximal end and a distal end, where the proximal end has an upper hub holding a first double-ended needle cannula and a connector configured for attachment to a drug delivery device. A bypass housing is located inside the outer housing that has one or more non-linear slots that rotatably and slidably engage radial protrusions or stand-offs on a locking disc and on a lower hub. There is a reservoir within the bypass housing comprising a single dose of a medicament. The medicated module assembly of our invention contains a needle guard that can reduce the risk of accidental needle sticks before and after use, reduce the anxiety of users suffering from needle phobia as well as preventing a user from using the device a subsequent time when the additional medicament has already been expelled.

The inner wall has a radial pin or stand-off that engages a non-linear track on an outside surface of a rotating cylinder. Radial protrusions on the inside surface of the cylinder engage the radial protrusions on the locking disc and lower hub. There is a also a biasing member engaged between the guard and the lower hub.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be from about 3 to about 4 mm. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent guard is used) while keeping the size small enough to prevent accidental needle stick injuries.

Further, the needle guard or shield is configured to move axially in both the distal and proximal directions when pressed against and removed from an injection site. When the needle assembly is removed or withdrawn from the patient, the guard is returned to post-use extended position. A locking mechanism on the guard, rotating cylinder, or combination of both can be used to securely lock the guard from further substantial axial movement at the completion of the injection. A locking mechanism could also be used to further lock the medicated module from any further use and prevent the needle(s). Likewise, there can be an additional locking mechanism that prevents the capsule from being able to substantially move within the system even if the guard is held in an axially locked condition. By "substantial" movement we do not mean the typical amount of "play" in a system, but instead we mean that the guard and/or distal needle do not move axially a distance that exposes the distal end of the cannula once it is locked out.

One goal of our invention is to eliminate the need to have the user manually operate the medicated module to change the state of the module from a priming state to a combination dose delivery state. Manually operated devices are sometimes not as intuitive as they could be and raise the risk of accidental misuse. Our invention solves this problem by utilizing a rotating cylinder that is moved by the retraction of needle guard thus activating the state change from prime dose to combination dose. The mechanism aims to make this actuation imperceptible to the user, consequently making the user experience of the module very similar to that of a standard commercially available and accepted needle or safety needle (i.e. unpack module, attach to a drug delivery device, prime drug delivery device, inject a set dose along with single dose in the module). In this way, the module mechanism aims to reduce the risk of unintentional misuse and to improve usability by replicating an already accepted practice for similar injection methods.

As the module mechanism does not require the user to access external features on the module for the purposes of actuation, the number of components and subsequent module size can be reduced/optimized. These factors make the mechanism ideal for a single-use, high-volume manufacture, and disposable device application. Alternatively, as the actuation is driven by a single action, the system lends itself to a resettable actuation mechanism. The preferred embodiment described below is the single use (non-resettable) version. The rotating cylinder in combination with a biasing force, preferably from a compression spring, causes the lower hub to rotate and then to move axially as the needle guard is retracted. The needle guard is restrained rotationally with regard to the outer housing, but is free to move axially, between defined constraints, within the outer housing.

The user pressing the distal face of the needle guard against the skin causes axial motion of the needle guard in the proximal direction. This axial motion of the guard causes a rotation of the cylinder through the engagement and action of an inward-facing drive tooth on the guard as it travels in a drive track having a non-linear path, which is located on the outer surface of the cylinder. After sufficient axial travel of the needle guard, the rotation of the cylinder causes the stand-offs inside the cylinder to rotate the lower hub. Likewise, the locking disc also rotates within pockets or slots located on the bypass housing. Rotation of the stand-offs within the pockets allows the locking disc to unlock and the reservoir to move proximally. The lower hub, which preferably contains a double-ended needle cannula, also rotates and moves axially as the rotating cylinder rotates. It is this axial movement of the lower hub that results in the double ended needles located in the outer body and the lower hub piercing the reservoir seals, moving it from a state of priming to combination dose delivery.

Further axial and proximal movement of the needle guard is required in order to pierce the skin, which compresses the biasing member creating a force that acts on the lower hub to result in the axial movement of the reservoir in the proximal direction. In normal use, once the drug has been dispensed and the needle is removed from the skin, the needle guard is allowed to return axially in the distal direction under the relaxation of the biasing member as it releases its stored energy. At some point along its return travel, a lock out mechanism is triggered locking out the needle guard from further use or exposing the needle. Should the user remove the device from the skin without dispensing fluid, but after the "commit" point has been passed, the needle guard would return to an extended position and lock out as previously described. In one embodiment of our invention there is provided a medicated module assembly as described herein attachable to a drug delivery device, preferably a pen shaped injection device, where the medicated module assembly comprises an outer housing having a proximal end and a distal end, where the proximal end has an upper hub holding a first double-ended needle cannula and a connector configured for attachment to a drug delivery device. The hub can be a separate part from the housing or integral, for example molded as part of the housing. The connector can be any connector design, such as threads, snap fits, bayonet, luer lock, or combination of these designs.

Preferably, two needle cannula are used, a distal cannula and a proximal cannula, with both cannulae preferably being doubled-ended for piercing a septum or seal and for piercing skin. The distal needle is mounted in a lower hub and the proximal needle is mounted in the upper hub of the outer housing, each using any technique known to those skilled in the art, such as welding, gluing, friction fit, over-molding and the like. The medicated module assembly also contains a biasing member, preferably a compression spring. The biasing member is preferably in a pre-compressed state and positioned between the proximal inner face of the needle guard and the distal face of the lower hub. Although a preferred biasing member is a spring, any type of member that produces a biasing force will work.

The medicated module assembly of our invention automatically, once triggered, changes state from (1) a pre-use or priming state, where a small amount of primary medicament flows in a bypass around the reservoir containing a single dose of the secondary medicament, to (2) a ready-to-use or combination dose state, where both the upper and lower cannulae are in fluidic engagement with the fixed dose of the second medicament within the module and where a set dose of the primary medicament can be injected along with the non-settable single dose of secondary medicament in the reservoir, and finally to (3) a locked out state, where the needle guard is prevented from substantial proximal movement. The outer housing preferably has a window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both a pre-use priming position and a locked position of the guard after the medicated module assembly has been used to perform an injection.

Inside the bypass housing there is a cavity that contains the reservoir or capsule, which comprises the single dose of medicament. As the needle guard is retracted during an injection, the capsule is moved proximally inside the cavity, thus decreasing the cavity volume. This reduction in volume caused by the axial movement of the capsule allows the seals of the capsule to be pierced at its top and bottom by the needle cannula such that the medicament can be expelled from the reservoir during dose delivery. When connected to a drug delivery device containing a first medicament and prior to piercing the seals of the capsule, the needle cannulae are only in fluid communication with the first medicament and a fluid flow path or bypass that bypasses the capsule. Preferably, a channel on the outside of the capsule or alternatively on the inside surface of the bypass housing is part of this fluid flow path and is used in the priming function of the drug delivery device.

As mentioned, the rotating cylinder preferably has one or more non-linear tracks located on the outside surface. On the inner surface of the proximal end of the needle guard is one or more radial protrusions or drive teeth. As the guard first begins to retract, these protrusions travel in the track on the rotating cylinder first linearly, then non-linearly to rotate the cylinder and then finally linearly where the cylinder does not rotate. The guard is rotationally constrained by the outer housing, preferably by the use of one or more ribs or pip features in the outer surface of the guard in cooperation with one or more splines or grooves located on the inner surface of the outer housing.

A further aspect of the invention relates to a method of dispensing a fixed dose of one medicament and a variable dose of a primary medicament from separate reservoirs that involves the steps of first attaching a medicated module to a delivery device set in a pre-use or prime only state. The user can prime the dose delivery device using only the primary medicament and bypassing the second medicament. After priming the user begins the injection and the needle guard begins to retract and the module automatically changes to second state that allows a combination delivery of the two medicaments. Upon completion of the delivery procedure and retraction of the needle from the injection site, the extension of the needle guard automatically changes the module to a third state.

During dispense, substantially the entire amount of second medicament has been expelled as well as the selected or dialed dose of the first medicament, through the single dispense interface. The reservoir preferably contains a flow distributor to ensure that substantially all the single dose of secondary medicament is forced out of the capsule by the primary medicament during an injection. The flow distributor can be a separate stand alone insert or pin. Alternatively the flow distributor and the capsule together can be manufactured or assembled as a one-piece component where the flow distributor is integral with the reservoir or capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably the capsule and/or flow distributor can be made from compatible materials of construction that include, but are not limited to, COC (an amorphous polymer based on ethylene and norbornene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g., glass, plastics or specific polymers, for example, TPE (thermo plastic elastomer); LSR (liquid silicone rubber); LDPE (low density polyethylene); and/or any kind of medical grade rubber, natural or synthetic.

By "substantially all" we mean that at least about 80% of the second medicament is expelled from the drug delivery device, preferably at least about 90% is expelled. In the third state, preferably the module is locked so as to prevent a second delivery or insertion by means of a locking mechanism.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module of our invention can be designed for use with any drug delivery device with an appropriate compatible interface. However, it may be preferable to design the module in such a way as to limit its use to one exclusive primary drug delivery device (or family of devices) through employment of dedicated/coded/exclusive features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary drug delivery device is used more than once and therefore is multi-use; however, the drug delivery device may also be a single use disposable device. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the patient attempt to reuse a previously used medicated module, our invention includes the locking needle guard that is activated after a first predefined travel/retraction of the guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature of our invention is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

Our invention also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

Exemplary embodiments are described herein with reference to the drawings, in which:

FIG. 1 illustrates one possible drug delivery device that can be used with the present invention;

FIG. 2 illustrates an embodiment of the medicated module of the present invention, where the medicated module is separated from an attachable cartridge holder of drug delivery device;

FIG. 10 is an exploded view of the capsule containing the second medicament of the embodiment of FIG. 3;

FIG. 11 is a perspective view of the reservoir showing part of the bypass of the embodiment of FIG. 3; and FIG. 12 is another perspective vie of the reservoir showing the flow distributor.

DETAILED DESCRIPTION

Figure 7:
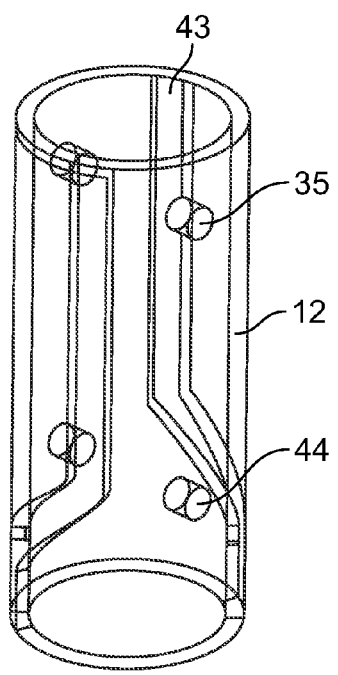
FIG. 7 is illustrates a transparent perspective view of the rotating cylinder of the embodiment of FIG. 3

The present invention administers a fixed predetermined dose of a secondary drug compound (medicament) and a variable dose of a primary or first drug compound through a single output or drug dispense interface. Setting the dose of the primary medicament by the user automatically determines the fixed dose of the second medicament, which preferably is a single dose contained in a capsule or reservoir having an integral flow distributor. In a preferred embodiment the drug dispense interface is a needle cannula (hollow needle). FIG. 1 illustrates one example of a drug delivery device 7 that the medicated module 4 (see FIG. 2 or 7) of our invention can be attached to the connection means 9 on cartridge holder 50 of distal end 32. Each medicated module is preferably self-contained and provided as a sealed and sterile disposable module that has an attachment means 8 compatible to the attachment means 9 at the distal end 32 of device 7. Although not shown, the medicated module could be supplied by a manufacturer in a protective and sterile container, where the user would peel or rip open a seal or the container itself to gain access to the sterile medicated module. In some instances it might be desirable to provide two or more seals for each end of the medicated module.

Figure 4:
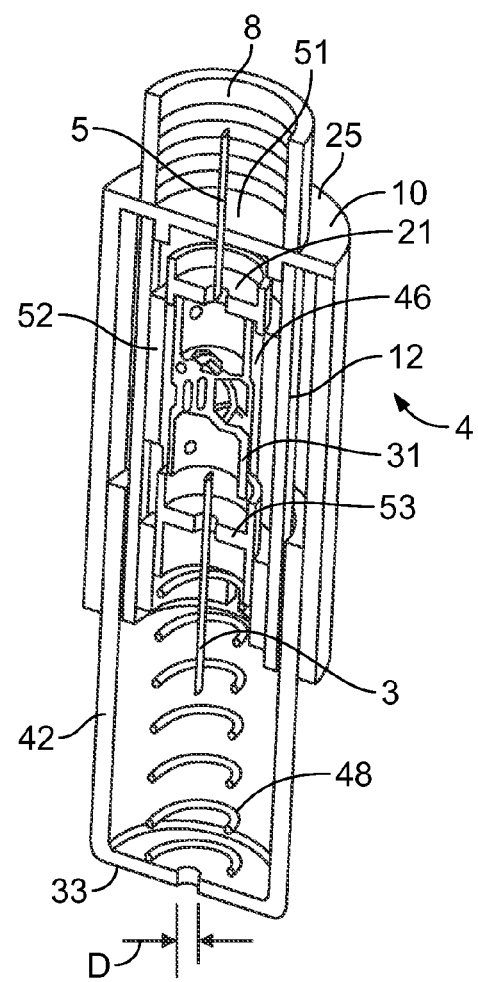
FIG. 4 illustrates a sectional view of select components of the medicated module illustrated in FIG. 3.

Any known attachment means 8 can be used to attach the medicated module to the chosen drug delivery device, including all types of permanent and removable connection means, such as threads, snap locks, snap fits, luer locks, bayonet, snap rings, keyed slots, and combinations of such connections. FIGS. 1 and 2 illustrate the attachment means 9 as threaded connection and also as a unique connection that is keyed specifically to a corresponding connection on medicated module 4, respectively. FIG. 4 shows the medicated module with a corresponding screw thread 8 associated with hub 51. The embodiment shown in FIG. 4 has the benefit of the second medicament as a single dose being contained entirely within capsule 31, and specifically in reservoir 22, hence minimizing the risk of material incompatibility between the second medicament and the materials used in the construction of the medicated module 4, specifically housing 10, inner housing 52, or any of the other parts used in the construction of the medicated module.

To minimize the residual volume of the second medicament, caused by recirculation and/or stagnant zones, that might remain in capsule 31 at the end of the dispense operation, it is preferable to have a flow distributor 23 as an integral part of reservoir 22 (see FIGS. 10 and 12). The reservoir 22 containing the single dose of the secondary medicament can be sealed with septa 6a and 6b, which are fixed to the capsule using keepers or plugs 20a and 20b. Preferably the keepers have fluid channels that are in fluid communication with needles 3 and 5 and with bypass 46, which is preferably part of the inside surface of bypass housing 52. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 should ensure that at least about 80% of the second medicament is expelled from reservoir 22 through the distal end of needle 3. Most preferably at least about 90% should be expelled. Ideally, displacement of the first medicament in a primary reservoir (not shown) contained in cartridge holder 50 and through the capsule 31 will displace the single dose of the second medicament stored in reservoir 22 without substantial mixing of the two medicaments.

Attachment of the medicated module 4 to the multi-use device 7 causes proximal needle 5 to penetrate a septum (not shown) sealing the distal end of the cartridge of primary medicament positioned in cartridge holder 50 of the multi-use device 7. Once needle 5 has passed through the septum of the cartridge, fluid connection is made between the first medicament and the needle 5. At this point, the system can be primed by dialing out a small number of units (or cocking the device if only a single dose selection is possible) using dose dial sleeve 62. Once the device 7 is primed, activation of the needle guard 42 allows dispense of the medicaments by subcutaneously injecting the medicaments via activation of a dose button 13 on device 7. The dose button of our invention can be any triggering mechanism that causes the dose of the first medicament that was set by the dose dial sleeve 62 to move towards the distal end 32 of the device. In a preferred embodiment the dose button is operably connected to a spindle that engages a piston in the primary reservoir of the first medicament. In a further embodiment the spindle is a rotatable piston rod comprising two distinct threads.

Figure 3:
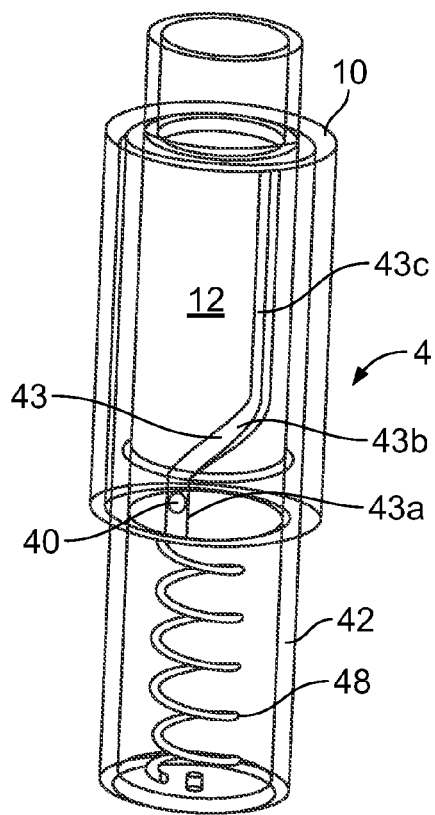
FIG. 3 illustrates a transparent view of one possible embodiment of the medicated module of our invention.

One embodiment of the medicated module 4 of our invention is illustrated in FIGS. 2, 3 and 4. In these embodiments the medicated module 4 contains a capsule 31 comprising a reservoir 22, two keepers 20a and 20b, and two seals 6a and 6b. Reservoir 22 contains a fixed single dose of a secondary medicament. In some cases this secondary medicament may be a mixture of two or more drug agents that can be the same or different from the primary drug compound in the drug delivery device 7. Preferably the capsule is permanently fixed within the medicated module, however, in some cases it may be preferred to design the module such that the capsule can be removed when empty and replaced with a new capsule.

In the embodiments shown in FIGS. 4 and 10, capsule 31 has ends that are sealed with pierceable membranes or septa 6a and 6b that provide a hermetically sealed and sterile reservoir 22 for the second medicament. A primary or proximal engagement needle 5 can be fixed in hub 51 connected to the proximal end of housing 10 of the module and configured to engage capsule 31 at some predetermined axial travel of the needle guard moving in the proximal direction during injection. The outlet, or distal needle 3, is preferably mounted in lower hub 53 and initially protrudes into lower keeper 20b (not shown in FIG. 4 for clarity reasons). The proximal end of needle 3 pierces the lower septum 6b as the lower hub is pushed by biasing member 48 in the proximal direction as the needle guard 42 is retracted a predetermined distance into outer housing 10 during injection.

When first attached to the delivery device, the medicated module 4 is set at a pre-use or starting position. Preferably, an indicator 41 shows through window 54 to inform the user of the pre-use condition of the medicated module. The indicator is preferably a color stripe or band on the outer surface of the proximal end of guard 42 (not shown) visible through an aperture 54 in the outer body. The needle guard 42 is slidably engaged with inner surface of outer housing 10 by engagement of rib 1 and channel 2 on the inside surface the outer housing. Of course, the rib and channel can be reversed as shown in FIG. 2 where channel 27 is located on the outside surface of needle guard 42. Preferably, retention snaps (not shown) prevent the guard from disengaging the outer housing at its fully extended position. Housing 10 partially defines bypass housing 52, which contains capsule 31. A portion of the proximal end of housing 10 defines an upper hub 51 that holds needle 5. Optionally, as illustrated in FIG. 4, a shoulder cap 25 may be added to the proximal outer surface of outer housing 10. This shoulder cap can be configured to serve as indicia to identify to a user the type/strength of medicament contained in the module. The indicia can be tactile, textual, color, taste or smell.

FIG. 4 shows a cutaway or cross-sectioned schematic view of the medicated module set in a pre-use or starting state where needles 3 and 5 are not piercing septa 6a and 6b. In this position, the lower hub 53, capsule 31 and locking disc 21 are at the most extended (or distally located) position and needles 3 and 5 are not in fluid communication with medicament contained in capsule 31. The capsule is supported by lower hub 53. In this neutral or suspended state of capsule 31, primary medicament from the cartridge in cartridge holder 50 of device 7 can flow through needle 5 into keeper 20a, through bypass 46 and into keeper 20b, and eventually out through needle 3. This flow configuration allows a user to perform a priming step or procedure by setting a small dose of the primary medicament using the dose dial sleeve 62 and dose button 13 on the drug delivery device 7.

Figure 5:
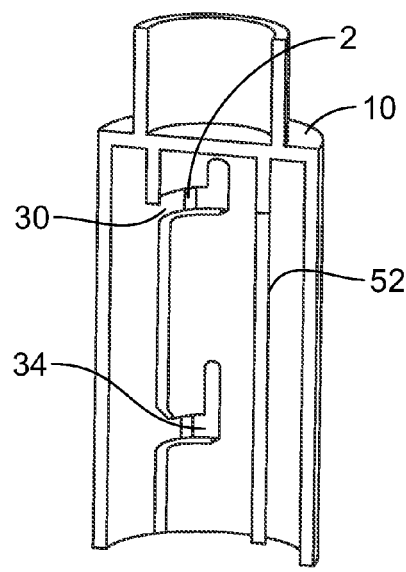
FIG. 5 is a sectional view of the outer housing and bypass cavity of the embodiment of FIG. 3.
Figure 6:
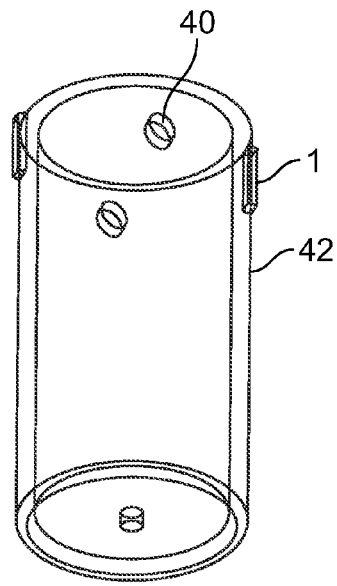
FIG. 6 illustrates a transparent perspective view of the needle guard of the embodiment of FIG. 3.
Figure 8:
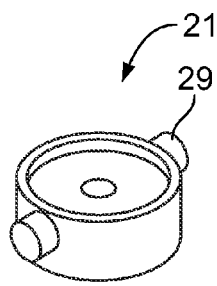
FIG. 8 is a close-up perspective view of the locking disc of the embodiment of the medicated module shown in FIG. 3.
Figure 9:
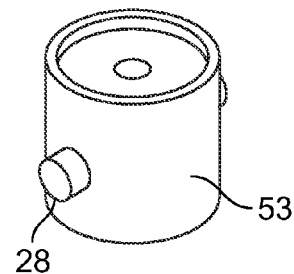
FIG. 9 is a close-up perspective view of the lower hub of the embodiment of the medicated module shown in FIG. 3.

The compression spring 48 is positioned between the distal end of lower hub 53 and the inner proximal face of guard 42 to bias the guard 42 into an extended (guarded) position as illustrated in FIGS. 3 and 4. Upon assembly, the proximal end of spring 48 positioned against lower hub 53, which is prevented from moving axially in the proximal direction by locking disc 21. The lower hub is prevented from moving axially by the engagement of the radial protrusions (28) with the slot in the bypass housing. The locking disc prevents the capsule from moving upwards into the proximal needle. As illustrated in FIG. 8, locking disc 21 has one or more radial protrusions 29 that engage slot 30 in bypass housing 52 (see FIG. 5). Because slot 30 is "L" shaped the locking disc cannot move proximally until the radial protrusion 29 is rotated to align with axial section of slot 30.

Likewise, the lower hub 53 has radial protrusions 28 that engage slot 34 in bypass housing 52 in the same manner as the radial protrusions 29 of locking disc 21. The combination of these radial protrusions and slots prevent the locking disc and lower hub from moving proximally and thereby preventing the needles from piercing into the centre of the capsule until the device is triggered as previously described.

The proximal inside surface of guard 42 has one or more inwardly protruding features, drive teeth, pips, or like structures 40 that run in one or more tracks 43 or guide ways formed in the outer surface of rotating cylinder 12. As shown in FIG. 3, track 43 can be described as three paths, 43a, 43b, and 43c, which have a specific geometry to make track 43 non-linear. As the needle guard 42 is pushed against an injection site it retracts proximally up into the outer housing 10, but is constrained from rotating by engagement of rib 1 with channel 2. Because pip 40 is engaged in track 43 and the needle guard cannot rotate, cylinder 12 is caused to rotate when pip 40 enters path 43b of track 43. As cylinder 12 rotates it causes both locking disc 21 and lower hub 53 to rotate through the engagement of radial protrusions 35 and 44 located on the inner surface of cylinder 12 (see FIG. 7) with radial protrusions 29 and 28, respectively. Once pip 40 exits path 43b and enters path 43c, the rotation of the locking disc and lower hub is complete and protrusions 29 and 28 enter the axial portions of slots 30 and 34, respectively. The needle guard 42 continues to move proximally with pip 40 continuing in track path 43c and spring 48 exerts a force on the distal end of lower hub 53 causing it, the reservoir 31, and the locking disc 21 to also move proximally. The engagement and configuration of the reservoir 31 with the lower hub 53 and locking disc 21 is selected to allow the lower hub to move a greater proximal distance than the reservoir so as to allow the proximal end of needle 3 to come into fluid communication with the second medicament.

One possible feature of our medicated module assembly is the inclusion of user feedback that is given when the assembly is used. In particular, the assembly could emit an audible and/or tactile "click" to indicate to the user that they have firstly triggered the device and secondly reached a "commit" point such that the needle guard will lock safely out upon completion of the injection/removal of the guard from the injection site.

As mentioned, the distal end of the guard 42 has a planar surface 33 that provides an added measure of safety and reduces the pressure exerted by the guard on the injection site during an injection with our needle assembly. Because the planar surface 33 substantially covers access to needle 3 a user is prevented from gaining access to the distal tip of the needle after the assembly is in the locked position. Preferably, the diameter D of needle pass through hole 21 in the planar surface is no more than 10 times that of the outer diameter of needle cannula 3.

The outer proximal surface of the needle guard 42 preferably has indicia (not shown) that are preferably at least two different color stripes or bands, each of which is sequentially visible through the opening or window 54 in outer housing 10. One color could designate the pre-use or prime state of the module and the other color would indicate that the module is in finished or locked state, another color could be used to denote the transition through the trigger or "commit" point in case a user stops injection after trigger point but before "commit" point. For example, a green color could be the pre-use position and a band of red color could be used to indicate that the module has been used and is locked and an orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that he needle guard is made form a transparent material.

In any of the above described embodiments of our invention the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

To minimize diffusion of the secondary medicament contained in the capsule within the medicated module into the primary medicament during dispense of the medicaments the reservoir 22 has an integral flow distributor 23. This flow distributor also ensures efficient expulsion of the second medicament from the system and greatly minimizes residual volume. One possible embodiment of the reservoir 22 and flow distributor 23 is illustrated in FIG. 12. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable, for example a material like COP. The flow distributor 23 is configured and positioned in reservoir 22 such that the secondary medicament fills flow channels that are defined by the shape and location of one or more channels (not shown) inside the reservoir. The shape of the flow channels can be optimized for a plug flow of medicament by varying the dimensions of the flow distributor and/or channels. The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of our invention should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, comprising,
    an outer housing having an inner surface, a proximal end and a distal end, where the proximal end comprises an upper hub holding a first double-ended needle cannula and a connector configured for attachment to a drug delivery device;

a locking disc comprising a radial protrusion;

a lower hub comprising a radial protrusion;

a bypass housing comprising non-linear slots that rotatably and slidably engage radial protrusion on the locking disc and the radial protrusion on the lower hub;

a reservoir within the bypass housing comprising a single dose of a medicament;

a rotating cylinder comprising an outer surface that comprises a non-linear track;

a guard having inner and outer walls, where the inner wall comprises a drive tooth that engages the non-linear track on the outside surface of the rotating cylinder, where an inside surface of the cylinder comprises radial protrusions that engage the radial protrusions on the locking disc and the radial protrusion on the lower hub, and a biasing member engaged between the guard and the lower hub.

2. The medicated module of claim 1 where the lower hub holds a second double-ended needle cannula.

3. The medicated module of claim 2 where the biasing member exerts a force on the lower hub when the guard is pushed in a proximal direction and locking disc becomes unlocked causing the reservoir to move in a proximal direction to come into fluid communication with the first and second double ended needle cannula.

4. The medicated module of claim 1 where a rib on the guard outer wall engages a channel on the inner surface of the outer housing to prevent the guard from rotating during linear movement relative to the outer housing.

5. The medicated module of claim 1 where the biasing member is a compressed spring.

6. The medicated module of claim 1 where the reservoir is a single molded component having an internal cavity with an integral flow distributor.

7. The medicated module of claim 1 where the non-linear track is configured such that axial movement of the needle guard causes the cylinder to rotate.

8. The medicated module of claim 7 where the rotation of the cylinder causes rotation of the locking disc and lower hub whereby the locking disc is unlocked allowing the reservoir to move proximally as the needle guard is retracted inside the outer housing.

9. The medicated module of claim 1 where the reservoir contains a liquid medicament.

10. The medicated module of claim 1 where the medicament in the reservoir comprises one of a GLP-1, an insulin, and a premix of insulin and a GLP-1.

11. The medicated module of claim 1 comprising a locked out state, where the needle guard is prevented from proximal movement wherein the extension of the needle guard automatically changes the module to this state.

12. A drug delivery system to deliver two or more medicaments operable through a single dispense interface, comprising, a primary reservoir of medicament containing at least one drug agent;

a dose button operably connected to the primary reservoir of medicament;

a single dispense interface configured for fluid communication with the primary reservoir; and the medicated module of claim 1.

* * * * *